(12) United States Patent
Nefzger et al.

(10) Patent No.: US 9,029,495 B2
(45) Date of Patent: May 12, 2015

(54) PROCESS FOR PRODUCING POLYETHER POLYOLS HAVING PRIMARY HYDROXYL END GROUPS

(75) Inventors: Hartmut Nefzger, Pulheim (DE); Erika Bauer, Jüchen (DE); Jörg Hofmann, Krefeld (DE); Klaus Lorenz, Dormagen (DE); Norbert Hahn, Frechen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 13/381,130

(22) PCT Filed: Jun. 30, 2010

(86) PCT No.: PCT/EP2010/003958
§ 371 (c)(1),
(2), (4) Date: Jan. 24, 2012

(87) PCT Pub. No.: WO2011/000560
PCT Pub. Date: Jan. 6, 2011

(65) Prior Publication Data
US 2012/0196999 A1    Aug. 2, 2012

(30) Foreign Application Priority Data
Jul. 3, 2009 (DE) .......... 10 2009 031 584

(51) Int. Cl.
| | | |
|---|---|---|
| *C08G 18/42* | (2006.01) | |
| *C08G 18/48* | (2006.01) | |
| *C08G 65/26* | (2006.01) | |
| *C08G 65/28* | (2006.01) | |
| *C07C 67/08* | (2006.01) | |
| *C07C 69/708* | (2006.01) | |
| *C07C 69/734* | (2006.01) | |
| *C08G 65/332* | (2006.01) | |
| *C07C 69/757* | (2006.01) | |
| *C07C 69/76* | (2006.01) | |
| *C07C 69/80* | (2006.01) | |
| *C07C 69/82* | (2006.01) | |

(52) U.S. Cl.
CPC ........ *C08G 18/4887* (2013.01); *C08G 65/2672* (2013.01); *C08G 65/3326* (2013.01); *C07C 67/08* (2013.01); *C07C 69/708* (2013.01); *C07C 69/734* (2013.01); *C07C 69/757* (2013.01); *C07C 69/76* (2013.01); *C07C 69/80* (2013.01); *C07C 69/82* (2013.01); *C08G 18/4866* (2013.01); *C08G 65/2615* (2013.01); *C08G 65/2663* (2013.01); *C08G 65/2669* (2013.01); *C08G 65/3324* (2013.01)

(58) Field of Classification Search
USPC ............. 252/182.26, 182.27, 182.28; 528/76, 528/80, 83; 560/91, 93, 96, 127, 198, 200, 560/205, 209; 568/607, 620, 623, 624

IPC ...... C08G 18/4887,18/4866, 65/2615, 65/2663, C08G 65/2672, 65/3324, 65/3326; C07C 67/08, C07C 69/708, 69/734, 69/757, 69/76, 69/80, C07C 69/82

See application file for complete search history.

(56) References Cited

U.S. PATENT DOCUMENTS

| | | | |
|---|---|---|---|
| 3,404,109 A | 10/1968 | Milgrom | |
| 3,829,505 A | 8/1974 | Herold | |
| 3,941,849 A | 3/1976 | Herold | |
| 4,487,853 A * | 12/1984 | Reichel et al. | 521/172 |
| 4,582,926 A | 4/1986 | Straehle et al. | |
| 5,158,922 A | 10/1992 | Hinney et al. | |
| 5,470,813 A | 11/1995 | Le-Khac | |
| 5,763,642 A * | 6/1998 | Cai | 560/198 |
| 6,066,683 A | 5/2000 | Beisner et al. | |
| 7,008,900 B1 | 3/2006 | Hofmann et al. | |
| 7,186,867 B2 | 3/2007 | Ostrowski et al. | |
| 2006/0105188 A1* | 5/2006 | Simons | 428/483 |
| 2008/0177025 A1* | 7/2008 | Hofmann | 528/412 |

FOREIGN PATENT DOCUMENTS

| | | |
|---|---|---|
| EP | 0248561 A1 | 12/1987 |
| EP | 0700949 A2 | 3/1996 |
| EP | 0743093 A1 | 11/1996 |
| EP | 0761708 A2 | 3/1997 |
| WO | WO-97/40086 A1 | 10/1997 |
| WO | WO-98/16310 A1 | 4/1998 |
| WO | WO-00/47649 A1 | 8/2000 |
| WO | WO-2006060273 A2 | 6/2006 |
| WO | WO 2011/075343 A1 * | 6/2011 |
| WO | WO 2011/137011 A1 * | 11/2011 |

OTHER PUBLICATIONS

O'Connor et al., Polyurethanes Expo 2001, Sep. 30-Oct. 3, 2011, 3 pages.
Ionescu, "Chemistry and Technology of Polyols for Polyurethanes", Rapra Technology Limited, 3 pages, 2005.

* cited by examiner

*Primary Examiner* — Rabon Sergent
(74) *Attorney, Agent, or Firm* — Drinker Biddle & Reath LLP

(57) ABSTRACT

The present invention relates to a process for producing polyether polyols having primary hydroxyl end groups, comprising the steps of reacting a starter compound containing active hydrogen atoms with an epoxide under double metal cyanide catalysis, reacting the resulting product with a cyclic carboxylic anhydride and reacting this resulting product with ethylene oxide in the presence of a catalyst containing at least one nitrogen atom per molecule, excluding non-cyclic, identically substituted tertiary amines. The invention further relates to polyether polyols obtainable by this process, compositions containing said polyols and polyurethane polymers based on said polyols.

15 Claims, No Drawings

PROCESS FOR PRODUCING POLYETHER POLYOLS HAVING PRIMARY HYDROXYL END GROUPS

CROSS-REFERENCE TO RELATED APPLICATIONS

This application is a national stage application (under 35 U.S.C. §371) of PCT/EP2010/003958, filed Jun. 30, 2010, which claims benefit of German application 10 2009 031 584.5, filed Jul. 3, 2010, both of which are incorporated herein by reference in their entirety for all their useful purposes.

BACKGROUND

The present invention relates to a process for producing polyether polyols having primary hydroxyl end groups, comprising the steps of reacting a starter compound containing active hydrogen atoms with an epoxide under double metal cyanide catalysis, reacting the resulting product with a cyclic carboxylic anhydride and reacting this resulting product with ethylene oxide in the presence of a catalyst containing at least one nitrogen atom per molecule, excluding non-cyclic, identically substituted tertiary amines. The invention further relates to polyether polyols obtainable by this process, compositions containing said polyols and polyurethane polymers based on said polyols.

Long-chain polyether polyols produced by double metal cyanide catalysis (DMC catalysis) are also known as IMPACT polyethers. The nature of the system is such that they contain predominantly secondary hydroxyl end groups. The use of ethylene/propylene oxide mixes (EO/PO) is possible only up to a certain proportion of EO; for that reason it is not possible to obtain long-chain polyether polyols containing predominantly primary hydroxyl end groups by the impact method. Instead such polyethers are obtained either by catalysing exclusively with conventional base catalysis (for example KOH) or in a two-stage procedure by polymerising an EO end block onto an IMPACT PO polyether obtained by DMC catalysis, optionally a PO/EO mixed polyether or a polyether having PO/EO mixed end blocks, under KOH catalysis.

The KOH method generally has the disadvantage that this catalyst has to be separated off by laborious means, for example by neutralisation and filtration. Furthermore, in the case of long-chain polyethers in particular, undesired olefinic end groups are formed as secondary products. Such olefinic end groups or allyl ether end groups reduce the functionality of these polyethers and make them more difficult to use in certain applications. They also lead to polyurethane (PUR) products, which are of a poorer quality.

U.S. Pat. No. 4,487,853 discloses a process for producing a polyether ester polyol with a high content of primary hydroxyl groups. In this process a) the reaction product of a condensate of a polyol with an alkylene oxide is reacted with a cyclic carboxylic acid and b) ethylene oxide at a temperature of 50° C. to 125° C. The condensate is obtained from a polyol having 2 to 8 hydroxyl groups and an equivalent weight of 30 to 45 and an alkylene oxide having 2 to 4 carbon atoms and mixtures thereof. The condensate has an equivalent weight of 500 to 10,000. Following reaction with the cyclic carboxylic anhydride a semiester is obtained. The reaction of a) with ethylene oxide takes place in the presence of an effective amount of an amine, oxide or divalent metal catalyst. The ratio of equivalents of the anhydride to equivalents of the condensate is in the range from approximately 1:1 to approximately 1:2 and the molar ratio of ethylene oxide to anhydride is in the range from approximately 2:1 to approximately 1.5:1. A polyurethane from the reaction of an organic polyisocyanate with such polyols is also disclosed.

However, U.S. Pat. No. 4,487,853 does not describe how polyether polyols produced under DMC catalysis can be converted into polyols having primary hydroxyl end groups with as little processing effort as possible. There is consequently still a need for alternative production processes for polyether polyols having primary hydroxyl end groups and in particular for such processes which convert polyethers produced with DMC catalysis.

DESCRIPTION OF EMBODIMENTS

The invention provides a process for producing polyether polyols having primary hydroxyl end groups, comprising the following steps:

1. Reacting a starter compound containing active hydrogen atoms with an epoxide of the general formula (1):

in which R1 denotes hydrogen, an alkyl radical or an aryl radical and with the proviso that ≥0 wt. % to ≤30 wt. %, relative to the total amount of the epoxide (1) used, are ethylene oxide, the reaction being performed in the presence of a double metal cyanide catalyst and the crude product of this reaction undergoing no further purification other than a possible distillation step;

2. Reacting the product obtained in step 1 with a cyclic carboxylic anhydride; and
3. Reacting the product obtained in step 2 with ethylene oxide in the presence of a catalyst containing at least one nitrogen atom per molecule, excluding non-cyclic, identically substituted tertiary amines.

Where the present invention refers to the production of polyether polyols as the end product, the term naturally encompasses such polyether polyols which as a consequence of the process according to the invention also contain ester units.

One advantage of the process according to the invention is that polyethers produced under DMC catalysis which even with high average molecular masses exhibit no difference or only a technically insignificant difference between the actual and the ideal OH functionality, react to form polyols having a relatively high proportion of primary OH groups. The overall process is simplified by the fact that removal of the catalyst after the first step is dispensed with.

Compounds having (number-average) molecular weights of ≥18 g/mol to ≤2000 g/mol and ≥1 to ≤8 hydroxyl groups are preferably used as starter compounds containing active hydrogen atoms in step 1. Examples thereof are ethylene glycol, diethylene glycol, triethylene glycol, 1,2-propylene glycol, dipropylene glycol, 1,4-butanediol, hexamethylene glycol, bisphenol A, bisphenol F, trimethylolpropane, glycerol, castor oil, pentaerythritol, sorbitol, cane sugar, degraded starch and/or water.

Such starter compounds containing active hydrogen atoms can moreover also be used which were produced by for example conventional alkali catalysis from the aforementioned low-molecular-weight starter compounds and which are oligomeric alkoxylation products having (number-average) molecular weights of ≥200 g/mol to ≤2000 g/mol.

The epoxide of the general formula (1) is a terminal epoxide with a substituent R1, which can be hydrogen, an alkyl radical or an aryl radical. In the context of the overall invention the term "alkyl" generally encompasses substituents from the group comprising n-alkyl such as methyl, ethyl or propyl, branched alkyl and/or cycloalkyl. In the context of the overall invention the term "aryl" generally encompasses substituents from the group comprising mononuclear carboaryl or heteroaryl substituents such as phenyl and/or polynuclear carboaryl or heteroaryl substituents. It is also possible for mixtures of various epoxides to be used in the process according to the invention, provided that the constituents of the epoxide mixture all fall under the general formula (1). If mixtures of various epoxides are used, it is also possible for the mixing ratio of the epoxides to be altered incrementally or continuously during metering.

The double metal cyanide catalysts that are suitable for step 1 of the process according to the invention preferably have the general formula $M^1_a[M^2(CN)_b(A)_c]_d \cdot f M^1_g X_z \cdot h(H_2O) \cdot e L$.

$M^1$ here is a metal ion selected from the group containing $Zn^{2+}$, $Fe^{2+}$, $Co^{3+}$, $Ni^{2+}$, $Mn^{2+}$, $Co^{2+}$, $Sn^{2+}$, $Pb^{2+}$, $Mo^{4+}$, $Mo^{6+}$, $Al^{3+}$, $V^{4+}$, $V^{5+}$, $Sr^{2+}$, $W^{4+}$, $W^{6+}$, $Cr^{3+}$ and/or $Cd^{2+}$. $M^2$ denotes a metal ion selected from the group containing $Fe^{2+}$, $Fe^{3+}$, $Co^{2+}$, $Co_{3+}$, $Mn_{2+}$, $Mn_{3+}$, $V^{4+}$, $V^{5+}$, $Cr^{2+}$, $Cr^{3+}$, $Rh^{3+}$, $Ru^{2+}$ and/or $Ir^{3+}$. $M^1$ and $M^2$ are identical or different.

A is an anion selected from the group containing halide, hydroxide, sulfate, carbonate, cyanide, thiocyanate, isocyanate, cyanate, carboxylate, oxalate and/or nitrate. X is an anion selected from the group containing halide, hydroxide, sulfate, carbonate, cyanide, thiocyanate, isocyanate, cyanate, carboxylate, oxalate and/or nitrate. L is a water-miscible ligand selected from the group containing alcohols, aldehydes, ketones, ethers, polyethers, esters, ureas, amides, nitriles and/or sulfides.

The counting variables a, b, c, d, g and z are selected so as to ensure the electroneutrality of the compound. Furthermore, e denotes the coordination number of the ligand, f a fraction or integer greater than or equal to 0 and h a fraction or integer greater than or equal to 0.

The DMC catalysts that are suitable for step 1 of the process according to the invention are known in principle from the prior art (U.S. Pat. No. 3,404,109, U.S. Pat. No. 3,829,505, U.S. Pat. No. 3,941,849 and U.S. Pat. No. 5,158,922). Improved, highly active DMC catalysts, which are described for example in U.S. Pat. No. 5,470,813, EP 0 700 949 A2, EP 0 743 093 A1, EP 0 761 708 A2, WO 97/40086 A1, WO 98/16310 A1 and WO 00/47649 A1, are preferably used. They have an exceptionally high activity and allow polyether polyols to be produced with very low catalyst concentrations. The highly active DMC catalysts described in EP 0 700 949 A2, which in addition to a double metal cyanide compound such as zinc hexacyanocobaltate(III) and an organic complex ligand such as tert-butanol also contain a polyether having a number-average molecular weight of greater than 500 g/mol, are a typical example.

The DMC catalyst in step 1 is preferably obtained in accordance with the teaching from EP 0 700 949 A2, to which reference is made in full extent. The catalyst can contain as components a double metal cyanide compound, in other words a reaction product of a water-soluble metal salt and a water-soluble metal cyanide salt, also an organic complexing agent L and ≥5 wt. % to ≤80 wt. %, relative to the amount of catalyst, of a polyether having a number-average molecular mass of ≥500 g/mol.

The catalyst can be used in a proportion of, for example, ≥1 ppm to ≤100 ppm and preferably ≥10 ppm to ≤50 ppm, relative to the total mass of starter compound and epoxide (1) used.

The DMC-catalysed reaction between the starter compound and the epoxide (1) in step 1 generally takes place at temperatures of ≥20° C. to ≤200° C., preferably in the range from ≥40° C. to ≤180° C., particularly preferably at temperatures from ≥50° C. to ≤150° C. The reaction can be performed at total pressures of 0.0001 to 20 bar.

The (number-average) molecular weights of the polyether polyols produced in step 1 of the process according to the invention can be ≥500 g/mol to ≤100,000 g/mol, preferably ≥1000 g/mol to ≤50,000 g/mol, particularly preferably ≥2000 g/mol to ≤20,000 g/mol.

The reaction in step 1 can be performed continuously or discontinuously, for example in a batch or semi-batch process.

In the process according to the invention it is provided that in step 1 the epoxide (1) contains at most 30 wt. % of ethylene oxide. It has been found that with higher ethylene oxide contents no satisfactory reaction products are obtained for further processing in the subsequent steps of the process.

Within the context of the present invention it is provided that the crude product of the reaction from step 1 undergoes no further purification other than a possible distillation step. This distillation step is thus optional. The distillation step can remove unreacted epoxide (1), for example, from the resulting polyol. Purification steps which are not used on the product would include filtration, solvent extraction or chromatographic purification. This is an advantage of the process according to the invention, as costly purification steps for polyether polyols produced by the KOH method are avoided. A special purification step is not necessary because the double metal cyanide catalysts can remain in the crude product without disrupting the subsequent reactions and because they are needed in only small quantities.

In step 2 of the process according to the invention the product from step 1, which has been purified only by distillation if at all, is reacted further. In this step terminal hydroxyl groups of the polyether polyol obtained are reacted with a cyclic carboxylic anhydride. Opening the anhydride group results in an ester bond to the polyether polyol and a further free carboxyl group. The reaction is optionally performed in the presence of a catalyst containing at least one nitrogen atom per molecule. This is preferably an organic molecule, so the catalyst is an organic amine. Non-cyclic, identically substituted tertiary amines are excluded, however. An example of one such unsuitable amine is triethylamine. If a catalyst is used it is advantageously the same catalyst as in the subsequent step 3.

The amount of nitrogen-containing catalyst, relative to the total mass of the reaction batch in step 2, can be for example ≥10 ppm to ≤10,000 ppm, preferably ≥50 ppm to ≤5000 ppm and more preferably ≥100 ppm to ≤2000 ppm. The reaction temperature in step 2 can be ≥70° C. to ≤150° C. and preferably ≥80° C. to ≤135° C.

Step 3 of the process according to the invention relates to the reaction of the product obtained in step 2 with ethylene oxide. Reacting the carboxyl groups of the polyether by means of a ring-opening reaction produces hydroxyalkyl groups. Preferably ≥80%, ≥90% or ≥95% of the carboxyl groups react with the epoxide, and a proportion of primary hydroxyl groups of ≥50 mol % to ≤100 mol % or ≥60 mol % to ≤85 mol % is obtained.

It is provided according to the invention that this reaction is performed in the presence of a catalyst containing at least one nitrogen atom per molecule. This is preferably an organic molecule, so the catalyst is an organic amine. Non-cyclic, identically substituted tertiary amines are however excluded according to the invention. An example of one such unsuitable amine is triethylamine.

The amount of nitrogen-containing catalyst, relative to the total mass of the reaction batch in step 3, can be for example ≥10 ppm to ≤10,000 ppm, preferably ≥50 ppm to ≤5000 ppm and more preferably ≥100 ppm to ≤2000 ppm. The reaction temperature in step 3 can be ≥70° C. to ≤150° C. and preferably ≥80° C. to ≤135° C.

This step advantageously follows immediately after step 2, such that the ethylene oxide is added to the reaction batch from step 2 on completion of the reaction with the cyclic carboxylic anhydride.

In one embodiment of the process according to the invention the starter compound used in step 1 is a poly(oxyalkylene) polyol with an average functionality of ≥2.0 to ≤5.0, a number-average molecular mass of ≥62 g/mol to ≤1000 g/mol and an OH value of ≥100 mg KOH/g to ≤1860 mg KOH/g. The average functionality can also be ≥2.3 to ≤4.0, the number-average molecular mass ≥100 g/mol to ≤500 g/mol and the OH value 200 mg KOH/g to ≤300 mg KOH/g. The OH value can be determined in accordance with the standard DIN 53240.

In a further embodiment of the process according to the invention R1 in the epoxide of the general formula (1) is hydrogen, methyl, ethyl, n-propyl, isopropyl, n-butyl, sec-butyl, isobutyl, tert-butyl, cyclohexyl and/or phenyl. R1 is preferably methyl. Then the epoxide used is propylene oxide. Mixtures of propylene oxide and ethylene oxide are likewise preferred, resulting in mixed polyether blocks. A plurality of mixtures of propylene oxide and ethylene oxide with various mixing ratios can also be used in succession.

In a further embodiment of the process according to the invention the double metal cyanide catalyst in step 1 comprises zinc, cobalt and tert-butanol. This catalyst preferably also comprises ≥5 wt. % to ≤80 wt. %, relative to the amount of catalyst, of a polyether with a number-average molecular mass of ≥500 g/mol. The proportion of polyether can also be ≥10 wt. % to ≤70 wt. % and particularly preferably ≥15 wt. % to ≤60 wt. %. Particularly suitable polyethers are for example polyether polyols with an average OH functionality of 2 to 8 and a number-average molecular mass of ≥1000 g/mol to ≤10,000 g/mol and preferably ≥1000 g/mol to ≤5000 g/mol. Poly(oxypropylene) polyols, in particular diols and/or triols, with a number-average molecular mass of ≥1000 g/mol to ≤4000 g/mol are cited by way of example.

In a further embodiment of the process according to the invention the cyclic carboxylic anhydride used in step 2 is selected from the group comprising phthalic anhydride, tetrahydrophthalic anhydride, succinic anhydride and/or maleic anhydride.

In a further embodiment of the process according to the invention the catalyst used in step 3 is selected from the group comprising:
(A) Amines of the general formula (2):

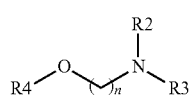

(2)

in which:
R2 and R3 are independently of each other hydrogen, alkyl or aryl; or
R2 and R3 together with the N-atom bearing them form an aliphatic, unsaturated or aromatic heterocycle;

n is a whole number from 1 to 10;
R4 is hydrogen, alkyl or aryl; or
R4 denotes —(CH$_2$)$_x$—N(R41)(R42), in which:
R41 and R42 are independently of each other hydrogen, alkyl or aryl;
or
R41 and R42 together with the N-atom bearing them form an aliphatic, unsaturated or aromatic heterocycle;
x is a whole number from 1 to 10;
(B) Amines of the general formula (3):

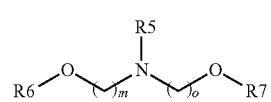

(3)

in which:
R5 is hydrogen, alkyl or aryl;
R6 and R7 are independently of each other hydrogen, alkyl or aryl;
m and o are independently of each other a whole number from 1 to 10;
and/or:
(C) Diazabicyclo[2.2.2]octane, diazabicyclo[5.4.0]undec-7-ene, dialkylbenzylamine, dimethylpiperazine, 2,2'-dimorpholinyldiethyl ether and/or pyridine.

The catalyst which can optionally be used in step 2 of the process can likewise be selected from groups (A), (B) and/or (C) described above.

Amines of the general formula (2) can be described in the broadest sense as amino alcohols or ethers thereof. If R4 is hydrogen then the catalysts can be incorporated into a polyurethane matrix if the polyether polyol is reacted with a polyisocyanate. This is advantageous as a means of preventing the escape of catalyst, which in the case of amines can be associated with disadvantageous odour problems, to the polyurethane surface, a phenomenon known as the fogging or VOC (volatile organic compounds) problem.

Amines of the general formula (3) can be described in the broadest sense as amino (bis)alcohols or ethers thereof. If R6 or R7 is hydrogen then these catalysts can likewise be incorporated into a polyurethane matrix.

It is preferred that in the amine of the general formula (2) R2 and R3 are methyl, R4 is hydrogen and n=2 or that R2 and R3 are methyl, R4 is —(CH$_2$)$_2$—N(CH$_3$)$_2$ and n=2. This therefore results overall in either N,N-dimethylethanolamine or bis(2-(dimethylamino)ethyl)ether.

It is further preferred that in the amine of the general formula (3) R5 is methyl, R6 and R7 are hydrogen, m=2 and o=2. This therefore results overall in N-methyldiethanolamine.

In a further embodiment of the process according to the invention the molar ratio in step 2 of cyclic anhydride to hydroxyl groups in the product obtained in step 1 is ≥0.75:1 to ≤1.3:1. The ratio is preferably ≥0.95:1 to ≤1.25:1, more preferably ≥1.02:1 to ≤1.15:1.

In a further embodiment of the process according to the invention the catalyst containing at least one nitrogen atom per molecule is present in step 3 in a proportion of ≥500 ppm to ≤1500 ppm relative to the total mass of the reaction batch in step 3. The proportion of catalyst can also be ≥750 ppm to ≤1250 ppm. The same applies correspondingly if such a catalyst is used in step 2 too.

In a further embodiment of the process according to the invention the molar ratio in step 3 of ethylene oxide to hydroxyl groups in the product obtained in step 1 is ≥0.90:1 to ≤5.0:1. The ratio can also be ≥1.0:1 to ≤2.0:1 or preferably ≥1.05:1 to ≤1.2:1.

The present invention also provides a polyether polyol having primary hydroxyl end groups, obtainable by a process according to the invention and comprising a polyether block, a terminal hydroxyethyl group and a diester unit linking the polyether block and the terminal hydroxyethyl group and wherein the molar proportion of terminal double bonds, relative to all end groups of the polyether polyol, is ≥0 milliequivalents per kg to ≤10 milliequivalents per kg. The polyether polyol is obtainable by a process according to the invention and in particular is obtained in this way. For that reason reference is made to the embodiments of the process in regard to details of its synthesis.

Without being limited thereto, the polyether block can for example be an ethylene oxide block, propylene oxide block, ethylene oxide/propylene oxide mixed block and/or any sequence of these blocks, started on a di-, tri-, tetra- or pentafunctional alcohol. The number of monomer units in the polyether block, in other words for example the number of ethylene oxide or propylene oxide units, can be in a range from ≥10 monomer units to ≤5000 monomer units, preferably ≥50 monomer units to ≤1000 monomer units.

A diester unit which can be attributed to the product of the reaction of an OH end group of the polyether block with a cyclic carboxylic anhydride is connected to the polyether block. In a ring-opening reaction a semiester is initially formed which then reacts with ethylene oxide to form the hydroxyethyl end group. Examples of the cyclic carboxylic anhydride are phthalic anhydride, tetrahydrophthalic anhydride, succinic anhydride and/or maleic anhydride.

The polyether polyol according to the invention is characterised in that the proportion of terminal double bonds, relative to all end groups of the polyether polyol (meaning the total number of polyether polyol molecules), is in the range from ≥0 to ≤10 milliequivalents per kg, regardless of the molar mass. For all practical purposes it is therefore free from unsaturated end groups. These end groups would reduce the functionality of the polyether and bring about corresponding disadvantages in the production of polyurethane polymers. Terminal double bonds are avoided for example by polymerising the polyether block onto the starter alcohol by means of DMC catalysis. The polyether polyol according to the invention can be checked for the absence of unsaturated end groups by $^1$H-NMR spectroscopy. Another common method is the determination of terminal double bonds using mercury acetate in accordance with ISO 17710. The content can also be ≥0 milliequivalents per kg to ≤5 milliequivalents per kg. Polyether polyols according to the invention can furthermore have functionalities in the range from ≥2 to ≤6 and molar masses in the range from ≥1800 Da to ≤20,000 Da.

In one embodiment of the polyether polyol according to the invention the molar proportion of primary hydroxyl groups is ≥50 mol % to ≤100 mol %. This is understood to be the molar proportion of primary hydroxyl groups as compared with secondary hydroxyl groups in the polyether polyol overall, in other words not relative to a single molecule. This can be determined by $^1$H-NMR spectroscopy, for example. The proportion can also be in a range from ≥55 mol % to ≤90 mol % or from ≥60 mol % to ≤85 mol %.

In a further embodiment of the polyether polyol according to the invention it has an OH value of ≥10 mg KOH/g to ≤100 mg KOH/g. The hydroxyl value can be determined by reference to the standard DIN 53240 and can also be ≥15 mg KOH/g to ≤80 mg KOH/g or ≥20 mg KOH/g to ≤50 mg KOH/g.

In a further embodiment of the polyether polyol according to the invention it has an acid value of ≥0.01 mg KOH/g to ≤5 mg KOH/g. The acid value can be determined by reference to the standard DIN 53402 and can also be ≥0.02 mg KOH/g to ≤4.9 mg KOH/g or ≥0.02 mg KOH/g to ≤4.8 mg KOH/g.

The present invention also provides a polyether polyol composition comprising a polyether polyol according to the invention and additionally:

(A) Amines of the general formula (4):

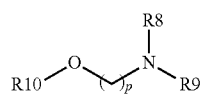

(4)

in which:
R8 and R9 are independently of each other hydrogen, alkyl or aryl; or
R8 and R9 together with the N-atom bearing them form an aliphatic, unsaturated or aromatic heterocycle;
p is a whole number from 1 to 10, i.e. 1, 2, 3, 4, 5, 6, 7, 8, 9 or 10;
R10 is hydrogen, alkyl or aryl; or
R10 denotes —(CH$_2$)$_y$—N(R11)(R12), in which:
R11 and R12 are independently of each other hydrogen, alkyl or aryl;
or
R11 and R12 together with the N-atom bearing them form an aliphatic, unsaturated or aromatic heterocycle;
y is a whole number from 1 to 10, i.e. 1, 2, 3, 4, 5, 6, 7, 8, 9 or 10;

(B) Amines of the general formula (5):

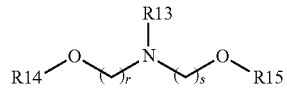

(5)

in which:
R13 is hydrogen, alkyl or aryl;
R14 and R15 are independently of each other hydrogen, alkyl or aryl;
r and s are independently of each other a whole number from 1 to 10, i.e. 1, 2, 3, 4, 5, 6, 7, 8, 9 or 10;
and/or:
(C) Diazabicyclo[2.2.2]octane, diazabicyclo[5.4.0]undec-7-ene, dialkylbenzylamine, dimethylpiperazine, 2,2'-dimorpholinyldiethyl ether and/or pyridine.

In certain variants such compounds can also be used as blowing catalysts, which means that they preferentially catalyse the reaction of the isocyanate groups with water to form carbon dioxide and to a lesser extent also their reaction with hydroxyl groups to form urethane groups. For that reason this composition can be used directly in the production of polyurethanes. If Zerewitinoff-active hydrogen atoms are present, these catalysts can be incorporated into a polyurethane matrix. This reduces the content of volatile organic compounds in the polyurethane. N,N-Dimethylethanolamine, bis(2-(dimethylamino)ethyl)ether or N-methyldiethanolamine are preferred.

The proportion of these compounds (A), (B) and/or (C) relative to the polyol according to the invention can be for example ≥10 ppm to ≤10,000 ppm, preferably ≥50 ppm to ≤5000 ppm and more preferably ≥100 ppm to ≤2000 ppm.

The present invention also provides a polyurethane polymer, obtainable from the reaction of a polyisocyanate with a polyether polyol according to the invention or a polyether polyol composition according to the invention. Also included according to the invention under the term "polyurethane polymer" are prepolymers obtainable from the reaction of a polyisocyanate with a polyether according to the invention or a polyether polyol composition according to the invention.

The present invention is illustrated in more detail by the examples below. The meanings and sources of the materials and abbreviations used are as follows:
2,2,2-Diazabicyclooctane (DABCO): Aldrich
N,N-Dimethylethanolamine (DMSA): Aldrich
Bis(2-(dimethylamino)ethyl)ether (DMAEE): Alfa Aesar
Triethylamine: Aldrich
Tetrahydrophthalic anhydride (THPA): Aldrich The analyses were performed as follows:
Viscosity: MCR 51 rheometer from Anton Paar
Determination of the molar proportion of primary OH groups: by $^1$H-NMR (Bruker DPX 400, deuterochloroform)
Hydroxyl value: by reference to DIN 53240
Acid value: by reference to DIN 53402

1. Production of the DMC-Catalysed Precursors:

Precursor A:

117.6 g of a poly(oxypropylene)triol with an OH value of 238 mg KOH/g and 0.024 g of DMC catalyst (produced in accordance with EP 0 700 949 A2) were placed in a 1-liter stainless steel pressure reactor under nitrogen, heated to 130° C. and then stripped for 30 minutes at 0.1 bar while passing nitrogen through the reactor. Then 682 g of propylene oxide were added at 130° C. within 3 hours. Following a post-reaction time at 130° C. to establish constant pressure in the reactor, highly volatile components were distilled off under vacuum at 90° C. for 30 minutes and the reaction mixture was then cooled to room temperature. The OH value of the product was 34.1 mg KOH/g at a viscosity (25° C.) of 967 mPas.

Precursor B:

117.6 g of a poly(oxypropylene)triol with an OH value of 238 mg KOH/g and 0.024 g of DMC catalyst (produced in accordance with EP 0 700 949 A2) were placed in a 1-liter stainless steel pressure reactor under nitrogen, heated to 130° C. and then stripped for 30 minutes at 0.1 bar while passing nitrogen through the reactor. Then a mixture of 504 g of propylene oxide and 38 g of ethylene oxide, followed by a mixture of 53 g of propylene oxide and 17 g of ethylene oxide and finally a mixture of 35 g of propylene oxide and 35 g of ethylene oxide were added at 130° C. within 3 hours. Following a post-reaction time at 130° C. to establish constant pressure in the reactor, highly volatile components were distilled off under vacuum at 90° C. for 30 minutes and the reaction mixture was then cooled to room temperature. The OH value of the product was 34.6 mg KOH/g at a viscosity (25° C.) of 954 mPas.

Precursor C:

117.6 g of a poly(oxypropylene)triol with an OH value of 238 mg KOH/g and 0.024 g of DMC catalyst (produced in accordance with EP 0 700 949 A2) were placed in a 1-liter stainless steel pressure reactor under nitrogen, heated to 130° C. and then stripped for 30 minutes at 0.1 bar while passing nitrogen through the reactor. Then a mixture of 439 g of propylene oxide and 33 g of ethylene oxide, followed by a mixture of 53 g of propylene oxide and 17 g of ethylene oxide, then a mixture of 35 g of propylene oxide and 35 g of ethylene oxide and finally a mixture of 21 g of propylene oxide and 49 g of ethylene oxide were added at 130° C. within 3 hours. Following a post-reaction time at 130° C. to establish constant pressure in the reactor, highly volatile components were distilled off under vacuum at 90° C. for 30 minutes and the reaction mixture was then cooled to room temperature. The OH value of the product was 35.3 mg KOH/g at a viscosity (25° C.) of 916 mPas.

Table 1 below summarises the data for precursors A, B and C.

|  |  | Precursor A | Precursor B | Precursor C |
|---|---|---|---|---|
| Polyoxypropylene triol | [g] | 117.6 | 117.6 | 117.6 |
| DMC catalyst | [g] | 0.024 | 0.024 | 0.024 |
| Propylene/ethylene oxide | [g/g] | 682/0 | 504/38 | 439/33 |
| Propylene/ethylene oxide | [g/g] |  | 53/17 | 53/17 |
| Propylene/ethylene oxide | [g/g] |  | 35/35 | 35/35 |
| Propylene/ethylene oxide | [g/g] |  |  | 21/49 |
| Proportion of ethylene oxide in total epoxide used | [wt. %] | 0 | 15 | 24 |
| OH value | [mg KOH/g] | 34.1 | 34.6 | 35.3 |
| Viscosity | [mPas, 25° C.] | 967 | 954 | 916 |

2. Reaction of DMC-Catalysed Precursors with Cyclic Anhydrides and Ethylene Oxide Under Amine Catalysis:

Example 1

Comparative Example 400 g of the DMC-catalysed precursor A, 40.66 g of tetrahydrophthalic anhydride and 0.462 g (1000 ppm, relative to the complete batch) of triethylamine were placed in a 1-liter stainless steel pressure reactor under nitrogen. The molar ratio of anhydride to the hydroxyl groups in precursor A was 1.1:1. Then the mixture was heated to 125° C. and stirred at this temperature for 3 hours. Then 21.42 g of ethylene oxide were metered into the reactor at 125° C. over a period of 30 minutes. The molar ratio of ethylene oxide to the hydroxyl groups in precursor A was 2:1. Following a post-reaction time at 125° C. to establish constant pressure in the reactor, highly volatile components were distilled off under vacuum at 90° C. for 30 minutes and the reaction mixture was then cooled to room temperature. The acid value of the product was 23.6 mg KOH/g at a viscosity (25° C.) of 4140 mPas. The very high acid value shows that only a small conversion with ethylene oxide occurred.

Example 2

400 g of the DMC-catalysed precursor A, 40.66 g of tetrahydrophthalic anhydride and 0.462 g (1000 ppm, relative to the complete batch) of DABCO (triethylenediamine) were placed in a 1-liter stainless steel pressure reactor under nitrogen. The molar ratio of anhydride to the hydroxyl groups in precursor A was 1.1:1. Then the mixture was heated to 125° C. and stirred at this temperature for 3 hours. Then 21.42 g of ethylene oxide were metered into the reactor at 125° C. over a period of 30 minutes. The molar ratio of ethylene oxide to the hydroxyl groups in precursor A was 2:1. Following a post-reaction time at 125° C. to establish constant pressure in the reactor, highly volatile components were distilled off under vacuum at 90° C. for 30 minutes and the reaction mixture was then cooled to room temperature.

Product Characteristics:
OH value: 28.2 mg KOH/g
Acid value: 2.58 mg KOH/g
Viscosity (25° C.): 3035 mPas
Primary OH groups: 65%

Example 3

400 g of the DMC-catalysed precursor A, 40.66 g of tetrahydrophthalic anhydride and 0.462 g (1000 ppm, relative to the complete batch) of bis(2-dimethylaminoethyl) ether were placed in a 1-liter stainless steel pressure reactor under nitrogen. The molar ratio of anhydride to the hydroxyl groups in precursor A was 1.1:1. Then the mixture was heated to 125° C. and stirred at this temperature for 3 hours. Then 21.42 g of ethylene oxide were metered into the reactor at 125° C. over a period of 30 minutes. The molar ratio of ethylene oxide to the hydroxyl groups in precursor A was 2:1. Following a post-reaction time at 125° C. to establish constant pressure in the reactor, highly volatile components were distilled off under vacuum at 90° C. for 30 minutes and the reaction mixture was then cooled to room temperature.

Product Characteristics:
OH value: 32.8 mg KOH/g
Acid value: 0.04 mg KOH/g
Viscosity (25° C.): 2685 mPas
Primary OH groups: 69%

Example 4

400 g of the DMC-catalysed precursor B, 37.54 g of tetrahydrophthalic anhydride and 0.459 g (1000 ppm, relative to the complete batch) of bis(2-dimethylaminoethyl)ether were placed in a 1-liter stainless steel pressure reactor under nitrogen. The molar ratio of anhydride to the hydroxyl groups in precursor B was 1:1. Then the mixture was heated to 125° C. and stirred at this temperature for 3 hours. Then 21.74 g of ethylene oxide were metered into the reactor at 105° C. over a period of 30 minutes. The molar ratio of ethylene oxide to the hydroxyl groups in precursor B was 2:1. Following a post-reaction time at 105° C. to establish constant pressure in the reactor, highly volatile components were distilled off under vacuum at 90° C. for 30 minutes and the reaction mixture was then cooled to room temperature.

Product Characteristics:
OH value: 32.8 mg KOH/g
Acid value: 0.05 mg KOH/g
Viscosity (25° C.): 2437 mPas
Primary OH groups: 73%

Example 5

400 g of the DMC-catalysed precursor B, 37.54 g of tetrahydrophthalic anhydride and 0.459 g (1000 ppm, relative to the complete batch) of bis(2-dimethylaminoethyl)ether were placed in a 1-liter stainless steel pressure reactor under nitrogen. The molar ratio of anhydride to the hydroxyl groups in precursor B was 1:1. Then the mixture was heated to 125° C. and stirred at this temperature for 3 hours. Then 21.74 g of ethylene oxide were metered into the reactor at 145° C. over a period of 30 minutes. The molar ratio of ethylene oxide to the hydroxyl groups in precursor B was 2:1. Following a post-reaction time at 145° C. to establish constant pressure in the reactor, highly volatile components were distilled off under vacuum at 90° C. for 30 minutes and the reaction mixture was then cooled to room temperature.

Product Characteristics:
OH value: 32.1 mg KOH/g
Acid value: 0.66 mg KOH/g
Viscosity (25° C.): 2229 mPas
Primary OH groups: 69%

Example 6

400 g of the DMC-catalysed precursor B, 41.29 g of tetrahydrophthalic anhydride and 0.463 g (1000 ppm, relative to the complete batch) of bis(2-dimethylaminoethyl)ether were placed in a 1-liter stainless steel pressure reactor under nitrogen. The molar ratio of anhydride to the hydroxyl groups in precursor B was 1.1:1. Then the mixture was heated to 125° C. and stirred at this temperature for 3 hours. Then 21.74 g of ethylene oxide were metered into the reactor at 105° C. over a period of 30 minutes. The molar ratio of ethylene oxide to the hydroxyl groups in precursor B was 2:1. Following a post-reaction time at 105° C. to establish constant pressure in the reactor, highly volatile components were distilled off under vacuum at 90° C. for 30 minutes and the reaction mixture was then cooled to room temperature.

Product Characteristics:
OH value: 32.2 mg KOH/g
Acid value: 0.53 mg KOH/g
Viscosity (25° C.): 2750 mPas
Primary OH groups: 74%

Example 7

400 g of the DMC-catalysed precursor B, 41.29 g of tetrahydrophthalic anhydride and 0.463 g (1000 ppm, relative to the complete batch) of bis(2-dimethylaminoethyl)ether were placed in a 1-liter stainless steel pressure reactor under nitrogen. The molar ratio of anhydride to the hydroxyl groups in precursor B was 1.1:1. Then the mixture was heated to 125° C. and stirred at this temperature for 3 hours. Then 21.74 g of ethylene oxide were metered into the reactor at 145° C. over a period of 30 minutes. The molar ratio of ethylene oxide to the hydroxyl groups in precursor B was 2:1. Following a post-reaction time at 145° C. to establish constant pressure in the reactor, highly volatile components were distilled off under vacuum at 90° C. for 30 minutes and the reaction mixture was then cooled to room temperature.

Product Characteristics:
OH value: 28.3 mg KOH/g
Acid value: 2.84 mg KOH/g
Viscosity (25° C.): 2525 mPas
Primary OH groups: 66%

Example 8

400 g of the DMC-catalysed precursor B, 41.29 g of tetrahydrophthalic anhydride and 0.463 g (1000 ppm, relative to the complete batch) of bis(2-dimethylaminoethyl)ether were placed in a 1-liter stainless steel pressure reactor under nitrogen. The molar ratio of anhydride to the hydroxyl groups in precursor B was 1.1:1. Then the mixture was heated to 125° C. and stirred at this temperature for 3 hours. Then 21.74 g of ethylene oxide were metered into the reactor at 90° C. over a period of 30 minutes. The molar ratio of ethylene oxide to the hydroxyl groups in precursor B was 2:1. Following a post-reaction time at 90° C. to establish constant pressure in the reactor, highly volatile components were distilled off under vacuum at 90° C. for 30 minutes and the reaction mixture was then cooled to room temperature.

Product Characteristics:
OH value: 28.2 mg KOH/g
Acid value: 2.41 mg KOH/g
Viscosity (25° C.): 3074 mPas
Primary OH groups: 75%

Example 9

200 g of the DMC-catalysed precursor B, 20.64 g of tetrahydrophthalic anhydride and 0.232 g (1000 ppm, relative to the complete batch) of bis(2-dimethylaminoethyl)ether were placed in a 1-liter stainless steel pressure reactor under nitrogen. The molar ratio of anhydride to the hydroxyl groups in precursor B was 1.1:1. Then the mixture was heated to 125° C. and stirred at this temperature for 3 hours. Then 6.0 g of ethylene oxide were metered into the reactor at 125° C. over a period of 30 minutes. The molar ratio of ethylene oxide to the hydroxyl groups in precursor B was 1.1:1. Following a post-reaction time at 125° C. to establish constant pressure in the reactor, highly volatile components were distilled off under vacuum at 90° C. for 30 minutes and the reaction mixture was then cooled to room temperature.

Product Characteristics:
OH value: 24.1 mg KOH/g
Acid value: 4.75 mg KOH/g
Viscosity (25° C.): 2578 mPas
Primary OH groups: 63%

Example 10

300 g of the DMC-catalysed precursor C, 31.59 g of tetrahydrophthalic anhydride and 0.348 g (1000 ppm, relative to the complete batch) of DABCO (triethylenediamine) were placed in a 1-liter stainless steel pressure reactor under nitrogen. The molar ratio of anhydride to the hydroxyl groups in precursor C was 1.1:1. Then the mixture was heated to 125° C. and stirred at this temperature for 3 hours. Then 16.63 g of ethylene oxide were metered into the reactor at 125° C. over a period of 30 minutes. The molar ratio of ethylene oxide to the hydroxyl groups in precursor C was 2:1. Following a post-reaction time at 125° C. to establish constant pressure in the reactor, highly volatile components were distilled off under vacuum at 90° C. for 30 minutes and the reaction mixture was then cooled to room temperature.

Product Characteristics:
OH value: 33.7 mg KOH/g
Acid value: 0.23 mg KOH/g
Viscosity (25° C.): 2760 mPas
Primary OH groups: 76%

Example 11

300 g of the DMC-catalysed precursor C, 31.59 g of tetrahydrophthalic anhydride and 0.348 g (1000 ppm, relative to the complete batch) of N,N-dimethylethanolamine were placed in a 1-liter stainless steel pressure reactor under nitrogen. The molar ratio of anhydride to the hydroxyl groups in precursor C was 1.1:1. Then the mixture was heated to 125° C. and stirred at this temperature for 3 hours. Then 16.63 g of ethylene oxide were metered into the reactor at 125° C. over a period of 30 minutes. The molar ratio of ethylene oxide to the hydroxyl groups in precursor C was 2:1. Following a post-reaction time at 125° C. to establish constant pressure in the reactor, highly volatile components were distilled off under vacuum at 90° C. for 30 minutes and the reaction mixture was then cooled to room temperature.

Product Characteristics:
OH value: 34.3 mg KOH/g
Acid value: 0.12 mg KOH/g
Viscosity (25° C.): 2274 mPas
Primary OH groups: 65%

Example 12

300 g of the DMC-catalysed precursor C, 31.59 g of tetrahydrophthalic anhydride and 0.348 g (1000 ppm, relative to the complete batch) of bis(2-dimethylaminoethyl) ether were placed in a 1-liter stainless steel pressure reactor under nitrogen. The molar ratio of anhydride to the hydroxyl groups in precursor C was 1.1:1. Then the mixture was heated to 125° C. and stirred at this temperature for 3 hours. Then 16.63 g of ethylene oxide were metered into the reactor at 125° C. over a period of 30 minutes. The molar ratio of ethylene oxide to the hydroxyl groups in precursor C was 2:1. Following a post-reaction time at 125° C. to establish constant pressure in the reactor, highly volatile components were distilled off under vacuum at 90° C. for 30 minutes and the reaction mixture was then cooled to room temperature.

Product Characteristics:
OH value: 34.6 mg KOH/g
Acid value: 0.06 mg KOH/g
Viscosity (25° C.): 2535 meas
Primary OH groups: 70%

Tables 2 below summarises the data for Examples 1 to 12:

|  |  | Example | | | |
| --- | --- | --- | --- | --- | --- |
|  |  | 1 (*) | 2 | 3 | 4 |
| Polyether polyol from precursor | Type | A | A | A | B |
|  | [g] | 400 | 400 | 400 | 400 |
| Cyclic carboxylic anhydride | Type | THPA | THPA | THPA | THPA |
|  | [g] | 40.66 | 40.66 | 40.66 | 37.54 |
| Molar ratio of anhydride to hydroxyl groups in polyether polyol | [mol/mol] | 1.1:1 | 1.1:1 | 1.1:1 | 1:1 |
| Catalyst | Type | NEt$_3$ | DABCO | DMAEE | DMAEE |
|  | [g] | 0.462 | 0.462 | 0.462 | 0.459 |
| Ethylene oxide | [g] | 21.42 | 21.42 | 21.42 | 21.74 |
| Molar ratio of ethylene oxide to hydroxyl groups in polyether polyol | [mol/mol] | 2:1 | 2:1 | 2:1 | 2:1 |
| Metering time for ethylene oxide | [min] | 30 | 30 | 30 | 30 |
| Metering temperature | [° C.] | 125 | 125 | 125 | 105 |
| Hydroxyl value | [mg KOH/g] | n.d. | 28.2 | 32.8 | 32.8 |

-continued

| | | | | | |
|---|---|---|---|---|---|
| Acid value | [mg KOH/g] | 23.6 | 2.58 | 0.04 | 0.05 |
| Viscosity | [mPas, 25° C.] | 4140 | 3035 | 2685 | 2437 |
| Hydroxyl groups, primary | [mol %] | n.d. | 65 | 69 | 73 |

| | | Example | | | |
|---|---|---|---|---|---|
| | | 5 | 6 | 7 | 8 |
| Polyether polyol from precursor | Type | B | B | B | B |
| | [g] | 400 | 400 | 400 | 400 |
| Cyclic carboxylic anhydride | Type | THPA | THPA | THPA | THPA |
| | [g] | 37.54 | 41.29 | 41.29 | 41.29 |
| Molar ratio of anhydride to hydroxyl groups in polyether polyol | [mol/mol] | 1:1 | 1.1:1 | 1.1:1 | 1.1:1 |
| Catalyst | Type | DMAEE | DMAEE | DMAEE | DMAEE |
| | [g] | 0.459 | 0.463 | 0.459 | 0.463 |
| Ethylene oxide | [g] | 21.74 | 21.74 | 21.74 | 21.74 |
| Molar ratio of ethylene oxide to hydroxyl groups in polyether polyol | [mol/mol] | 2:1 | 2:1 | 2:1 | 2:1 |
| Metering time for ethylene oxide | [min] | 30 | 30 | 30 | 30 |
| Metering temperature | [° C.] | 145 | 105 | 145 | 90 |
| Hydroxyl value | [mg KOH/g] | 32.1 | 32.2 | 28.3 | 28.2 |
| Acid value | [mg KOH/g] | 0.66 | 0.53 | 2.84 | 2.41 |
| Viscosity | [mPas, 25° C.] | 2229 | 2750 | 2525 | 3074 |
| Hydroxyl groups, primary | [mol %] | 69 | 74 | 66 | 75 |

| | | Example | | | |
|---|---|---|---|---|---|
| | | 9 | 10 | 11 | 12 |
| Polyether polyol from precursor | Type | B | C | C | C |
| | [g] | 200 | 300 | 300 | 300 |
| Cyclic carboxylic anhydride | Type | THPA | THPA | THPA | THPA |
| | [g] | 20.64 | 31.59 | 31.59 | 31.59 |
| Molar ratio of anhydride to hydroxyl groups in polyether polyol | [mol/mol] | 1.1:1 | 1.1:1 | 1.1:1 | 1.1:1 |
| Catalyst | Type | DMAEE | DABCO | DMEA | DMAEE |
| | [g] | 0.232 | 0.348 | 0.348 | 0.348 |
| Ethylene oxide | [g] | 6 | 16.63 | 16.63 | 16.63 |
| Molar ratio of ethylene oxide to hydroxyl groups in polyether polyol | [mol/mol] | 1.1:1 | 2:1 | 2:1 | 2:1 |
| Metering time for ethylene oxide | [min] | 30 | 30 | 30 | 30 |
| Metering temperature | [° C.] | 125 | 125 | 125 | 125 |
| Hydroxyl value | [mg KOH/g] | 24.1 | 33.7 | 34.3 | 34.6 |
| Acid value | [mg KOH/g] | 4.75 | 0.23 | 0.12 | 0.06 |
| Viscosity | [mPas, 25° C.] | 2578 | 2760 | 2274 | 2535 |
| Hydroxyl groups, primary | [mol %] | 63 | 76 | 65 | 70 |

(*): Comparative example

It is clear from the very low acid values in the end products of the examples according to the invention that scarcely any free carboxyl groups which form after the opening of the cyclic anhydride did not react with ethylene oxide. Furthermore, a comparison of the hydroxyl values of the end products and of the precursor polyethers A, B and C used at the start shows that only a slight increase in the molecular weights of precursors A, B and C occurred as a result of the process according to the invention. Finally the results show that primary end groups were obtained in each case in a proportion of over 50%.

The invention claimed is:

1. A process for producing polyether polyols having primary hydroxyl end groups, comprising the following steps:
   1. reacting a starter compound comprising active hydrogen atoms with an epoxide of the general formula (1):

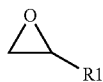
   (1)

wherein R1 represents hydrogen, an alkyl radical or an aryl radical and with the proviso that from 0 to 30 wt. %, relative to the total amount of the epoxide (1) used, are ethylene oxide, and
   wherein the reaction is performed in the presence of a catalyst comprising double metal cyanide, and optionally, purifying the crude product of the reaction in a distillation step;
   2. reacting the product obtained in step 1 with a cyclic carboxylic anhydride; and
   3. reacting the product obtained in step 2 with ethylene oxide in the presence of a catalyst
   selected from the group consisting of:
   (A) amines of the general formula (2):

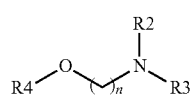
   (2)

wherein:
   R2 and R3 represent independently of each other hydrogen, alkyl or aryl; or
   R2 and R3 together with the N-atom bearing them form an aliphatic, unsaturated or aromatic heterocycle;
   n represents a whole number from 1 to 10;
   R4 represents hydrogen, alkyl or aryl; or R4 represents —(CH$_2$)$_x$—N(R41)(R42), in which:
  R41 and R42 are independently of each other hydrogen, alkyl or aryl; or R41 and R42 together with the N-atom bearing them form an aliphatic, unsaturated or aromatic heterocycle;
  x represents a whole number from 1 to 10; and
(B) amines of the general formula (3):

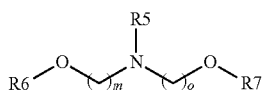
(3)

wherein:
  R5 represents hydrogen, alkyl or aryl;
  R6 and R7 represent independently of each other hydrogen, alkyl or aryl;
  m and o represent independently of each other a whole number from 1 to 10.

2. The process according to claim 1, wherein the starter compound used in step 1 is a poly(oxyalkylene) polyol with an average functionality of from 2.0 to 5.0, a number-average molecular mass of from 62 to 1000 g/mol and an OH value of from 100 to 1860 mg KOH/g.

3. The process according to claim 1, wherein R1 in the epoxide of the general formula (1) represents hydrogen, methyl, ethyl, n-propyl, isopropyl, n-butyl, sec-butyl, isobutyl, tert-butyl, cyclohexyl and/or phenyl.

4. The process according to claim 1, wherein the double metal cyanide catalyst in step 1 comprises zinc, cobalt and tert-butanol.

5. The process according to claim 1, wherein the cyclic carboxylic anhydride used in step 2 is selected from the group consisting of phthalic anhydride, tetrahydrophthalic anhydride, succinic anhydride, maleic anhydride, and combinations thereof.

6. The process according to claim 1, wherein the molar ratio in step 2 of cyclic anhydride to hydroxyl groups in the product obtained in step 1 is from 0.75:1 to 1.3:1.

7. The process according to claim 1, wherein the catalyst is present in step 3 in an amount of from 500 to 1500 ppm relative to the total mass of the reaction batch in step 3.

8. The process according to claim 1, wherein the molar ratio in step 3 of ethylene oxide to hydroxyl groups in the product obtained in step 1 is from 0.90:1 to 5.0:1.

9. A polyether polyol having primary hydroxyl end groups, obtained by the process according to claim 1, comprising a polyether block, a terminal hydroxyethyl group and a diester unit linking the polyether block and the terminal hydroxyethyl group and wherein the molar proportion of terminal double bonds, relative to all end groups of the polyether polyol, is from 0 to 10 milliequivalents per kg.

10. The polyether polyol according to claim 9, wherein the molar proportion of primary hydroxyl groups is from 50 to 100 mol %.

11. The polyether polyol according to claim 9 wherein the polyether polyol has an OH value of from 10 to 100 mg KOH/g.

12. The polyether polyol according to claim 9 wherein the polyether polyol has an acid value of from 0.01 to 5 mg KOH/g.

13. A polyether polyol composition comprising a polyether polyol according to claim 9.

14. A polyurethane polymer obtained by reacting at least a polyisocyanate with the polyether polyol according to claim 9.

15. A polyurethane polymer obtained by reacting at least a polyisocyanate with the polyether polyol composition according to claim 13.

* * * * *